(12) United States Patent
Bradin (10) Patent No.: US 9,422,494 B2
(45) Date of Patent: Aug. 23, 2016

(54) PROCESS FOR PRODUCING RENEWABLE JET FUEL COMPOSITIONS

(71) Applicant: David Bradin, Chapel Hill, NC (US)

(72) Inventor: David Bradin, Chapel Hill, NC (US)

(*) Notice: Subject to any disclaimer, the term of this patent is extended or adjusted under 35 U.S.C. 154(b) by 188 days.

(21) Appl. No.: 14/323,452

(22) Filed: Jul. 3, 2014

(65) Prior Publication Data

US 2015/0247100 A1  Sep. 3, 2015

Related U.S. Application Data

(60) Provisional application No. 61/842,477, filed on Jul. 3, 2013.

(51) Int. Cl.

| | | |
|---|---|---|
| *C07C 1/04* | (2006.01) | |
| *C07C 1/12* | (2006.01) | |
| *C07C 1/207* | (2006.01) | |
| *C07C 1/24* | (2006.01) | |
| *C07C 2/06* | (2006.01) | |
| *C07C 5/02* | (2006.01) | |
| *C07C 5/22* | (2006.01) | |
| *C10L 1/04* | (2006.01) | |
| *C07C 41/09* | (2006.01) | |
| *C10G 50/00* | (2006.01) | |
| *C07C 29/151* | (2006.01) | |
| *C10G 69/12* | (2006.01) | |
| *C10G 3/00* | (2006.01) | |

(52) U.S. Cl.
CPC ... *C10L 1/04* (2013.01); *C07C 1/24* (2013.01); *C07C 29/1518* (2013.01); *C07C 41/09* (2013.01); *C10G 3/49* (2013.01); *C10G 50/00* (2013.01); *C10G 69/126* (2013.01); *C10G 2300/1014* (2013.01); *C10G 2400/08* (2013.01); *C10J 2300/1665* (2013.01); *Y02E 20/18* (2013.01); *Y02E 50/18* (2013.01)

(58) Field of Classification Search
CPC ............. C07C 1/04; C07C 1/12; C07C 1/207; C07C 1/24; C07C 2/06; C07C 5/02; C07C 5/22; C10L 1/14; C10L 1/16; C10L 1/18
USPC ......... 585/302, 304, 319, 324, 326, 327, 329, 585/639, 469, 251, 502, 242; 208/15, 16, 208/17
See application file for complete search history.

(56) References Cited

U.S. PATENT DOCUMENTS 4,994,498 A * 2/1991 Kinkade ............... C07C 29/153
502/220

* cited by examiner

*Primary Examiner* — Thuan D Dang
(74) *Attorney, Agent, or Firm* — James G. Passé; Passé Intellectual Property, LLC (57) ABSTRACT

The present invention provides a process for producing jet fuel components from syngas. Syngas is converted to methanol and ethanol, and, optionally, higher alcohols. The methanol is separated from the ethanol and higher alcohols, and converted to $C_{5-9}$ paraffins and aromatics via a dimethyl ether intermediate. The dimethyl ether is reacted over a catalyst to form jet fuel range hydrocarbons and aromatics. The ethanol and higher alcohols are dehydrated to form olefins, which are then oligomerized and, optionally, hydrogenated and/or isomerized, to form products in the jet fuel range. All or part of the two separate product streams can be combined, to provide jet fuel components which include aromatics and paraffins, ideally isoparaffins, in the jet fuel range. The syngas is in one embodiment derived from biomass or another renewable carbon-containing feedstock, thereby providing a biorefining process for producing renewable jet fuel.

7 Claims, 1 Drawing Sheet

PROCESS FOR PRODUCING RENEWABLE JET FUEL COMPOSITIONS

This application claims priority of U.S. provisional application No. 61/842,477 filed on Jul. 3, 2013 and is incorporated in its entirety by reference.

FIELD OF THE INVENTION

The present invention generally relates to processes for the conversion of synthesis gas into renewable liquid fuels, including gasoline.

BACKGROUND OF THE INVENTION

Synthesis gas, which is also known as syngas, is a mixture of gases comprising carbon monoxide (CO) and hydrogen ($H_2$). Generally, syngas may be produced from any carbonaceous material. In particular, biomass such as agricultural wastes, forest products, grasses, and other cellulosic material may be converted to syngas.

Syngas is a platform intermediate in the chemical and biorefining industries and has a vast number of uses. Syngas can be converted into alkanes, olefins, oxygenates, and alcohols such as ethanol. These chemicals can be blended into, or used directly as, diesel fuel, gasoline, and other liquid fuels. Syngas can also be directly combusted to produce heat and power. The substitution of alcohols and/or derivatives of alcohols in place of petroleum-based fuels and fuel additives can be particularly environmentally friendly when the alcohols are produced from feed materials other than fossil fuels.

In recent years, considerable research has been devoted to providing alternative sources and manufacturing routes for jet fuels in recognition of the fact that petroleum is a non-renewable resource and that petroleum-based fuels such as gasoline and distillate will ultimately become more expensive.

A major development within the chemical/petroleum industry has been the discovery of the special catalytic capabilities of a family of zeolite catalyst based upon medium-pore size shape selective metallosilicates. Discoveries have been made leading to a series of analogous processes drawn from the catalytic capability of zeolites. Depending upon various conditions of space velocity, temperature, and pressure, methanol can be converted in the presence of zeolite-type catalysts to olefins which can oligomerize to provide gasoline or distillate, or can be converted further to produce aromatics.

It has been demonstrated that alcohols, ethers, and carbonyl-containing compounds can be converted to higher hydrocarbons, particularly aromatics-rich high-octane gasoline, by catalytic conversion employing a shape-selective medium pore acidic zeolite catalyst such as H-ZSM-5. This conversion is described in, among others, U.S. Pat. Nos. 3,894,103; 3,894,104; 3,894,106; 3,907,915; 3,911,041; 3,928,483; and, 3,969,426. The conversion of methanol to gasoline in accordance with this technology (the "MTG" process) produces mainly $C_{5+}$ gasoline-range hydrocarbon products together with $C_3$-$C_4$ gases and $C_9$ heavy aromatics. The desirable $C_6$-$C_8$ aromatics (principally benzene, toluene and xylenes) can be recovered as a separate product slate by conventional distillation and extraction techniques.

Traditional approaches for converting syngas to gasoline involve a two-step process comprising converting syngas to methanol followed by converting methanol to gasoline. What are needed, in view of the art and commercial drivers, are process configurations, apparatus, and suitable catalysts for conversion of syngas into gasoline components as well as oxygenates, such as alcohols, for blending into oxygenated gasoline. Additionally, methods that proceed through higher alcohols (ethanol and heavier) are desired in order to take advantage of the state of the art for ethanol synthesis and higher-alcohol synthesis from syngas.

SUMMARY OF THE INVENTION

In one embodiment, the present invention relates to a process for producing jet fuel components. The process comprises:
(a) generating or providing syngas;
(b) converting the syngas using an alcohol-synthesis catalyst to a first stream comprising methanol, ethanol, and, optionally, higher alcohols;
(c) separating the methanol from the ethanol and, optionally, higher alcohols,
(d) converting at least some of the methanol to dimethyl ether,
e) converting the dimethyl ether to one or more jet fuel range hydrocarbons and aromatics using a zeolite catalyst,
f) dehydrating the ethanol and, optionally, higher alcohols to form ethylene and, optionally, higher olefins,
g) oligomerizing the ethylene and, optionally, higher olefins to produce olefins in the jet fuel range,
h) hydrogenating the olefins in the jet fuel range to form paraffins in the jet fuel range, and
i) combining one or more products from step c) with one or more of the products of step h).

The syngas can be derived, for example, from biomass such as wood chips or from any other carbon-containing feedstock.

The jet fuel components are not particularly limited but can include at least one $C_{5-10}$ hydrocarbon. Jet fuel components can include branched hydrocarbons, olefins, and aromatics.

Certain methods of the invention further include hydrotreating, isomerizing, or otherwise catalytically treating at least some of the jet fuel components.

The jet fuel components can be used directly as jet fuel, or blended with another fuel to generate commercial jet fuel.

In another embodiment, the invention relates to jet fuel compositions. In one aspect of this embodiment, a composition comprises the jet fuel components produced in accordance with any of the methods described herein. In some embodiments, a composition consists essentially of the jet fuel components produced in accordance with any of the methods described herein. In other embodiments, the jet fuel compositions comprise one or more conventional jet fuel compositions, such as JP8, JetA, JP1, and the like, to which one or more of the components produced according to the methods described herein are added.

These and other embodiments, features, and advantages of the present invention will become more apparent to those skilled in the art when taken with reference to the following detailed description of the invention in conjunction with the accompanying drawings.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are herein incorporated by reference, the definition set forth in this specification prevails over the definition that is incorporated herein by reference.

Variations of this invention are premised, at least in part, on the conversion of syngas into methanol, ethanol, and, optionally, one or more higher alcohols. A "higher alcohol," as used herein, means a $C_3$, $C_4$, $C_5$, or higher alcohol, but the majority of higher alcohols are $C_{3-5}$, more predominantly, $C_{3-4}$ alcohols.

Jet fuel components include any molecule capable of being combusted in a jet fuel engine to provide power for an airplane or other machine burning jet fuel for energy. Jet fuel components include alkanes, olefins, cyclic hydrocarbons, and aromatics.

Some variations of the invention relate to an integrated biorefinery capable of producing one or more liquid transportation fuels, including oxygenated fuels. In some embodiments, the invention provides a process that converts syngas into jet fuel components. In some embodiments, the invention provides a process that converts syngas into alcohol fuels such as methanol, ethanol, propanol, butanol, and/or heavier alcohols, including various isomers. Once methanol is removed from ethanol and the higher alcohols, at least a portion of the methanol is converted to dimethyl ether (DME), which is then chemically converted into jet fuel components.

In some variations, syngas is produced or otherwise provided in a biorefinery. The syngas can be divided into a plurality of streams and fed to several unit operations. Biorefinery optimization can be carried out to adjust the splits to the different units, for economic reasons. Syngas can be a fuel itself to provide internal process energy, or sold directly as a co-product, or converted into electricity for external sale. At least a portion of the syngas, in the context of the present invention, is converted to liquid fuels.

Engineering optimization can be conducted to achieve energy integration. For example, energy requirements for product separations can be reduced by combining portions of the product streams from individual processes into a single unit, such as distillation and drying. Various levels of heat recovery can be employed to meet drying and separation requirements.

Also, specifications on intermediate streams can be relaxed to reduce energy requirements. In some embodiments, mixed alcohols or individual alcohol streams are partially or completely dried for feeding into an alcohols-to-jet fuel step, thereby reducing drying requirements and costs. In some embodiments, a methanol stream is allowed to contain ethanol in excess of that described in an ASTM specification, such as 1-2 vol %, for feeding to a methanol-to-dimethyl ether step, thereby reducing energy costs. In some embodiments, ethanol and higher alcohols are fed to an alcohol dehydration step.

In the present invention, alcohols larger than methanol are used to conduct the reactions to produce olefinic precursors of jet fuel. Alcohols such as ethanol, propanol, butanol, and $C_{5+}$ alcohols (including all isomers) are desirable in some embodiments.

Various embodiments of the invention produce one or more jet fuel components selected from the group consisting of 2-methylbutane, 4-methylpentene, methylcyclopentane, benzene, toluene, ethylbenzene, m-xylene, p-xylene, o-xylene, 1-ethyl-4-methylbenzene, 1,2,4-trimethylbenzene, 1-methyl-4-(ethylmethyl)-benzene, 1,2-diethylbenzene, 1-ethyl-2,4-dimethylbenzene, 2,3-dihydro-1-methyl-1-indene, naphthalene, 2-methylnaphthalene, 1,8-dimethylnaphthalene, 2-(1-methylethyl)- and naphthalene. Other alkanes, olefins, cyclic hydrocarbons, and aromatics can be produced.

Also, in some embodiments, light components (such as methane, ethane, and propane) may be recovered as fuel gas suitable for energy requirements within the biorefinery. In certain embodiments, crude jet fuel components may be distilled to produce a fuel-grade LPG-type stream and a jet fuel stream.

Figure 1:
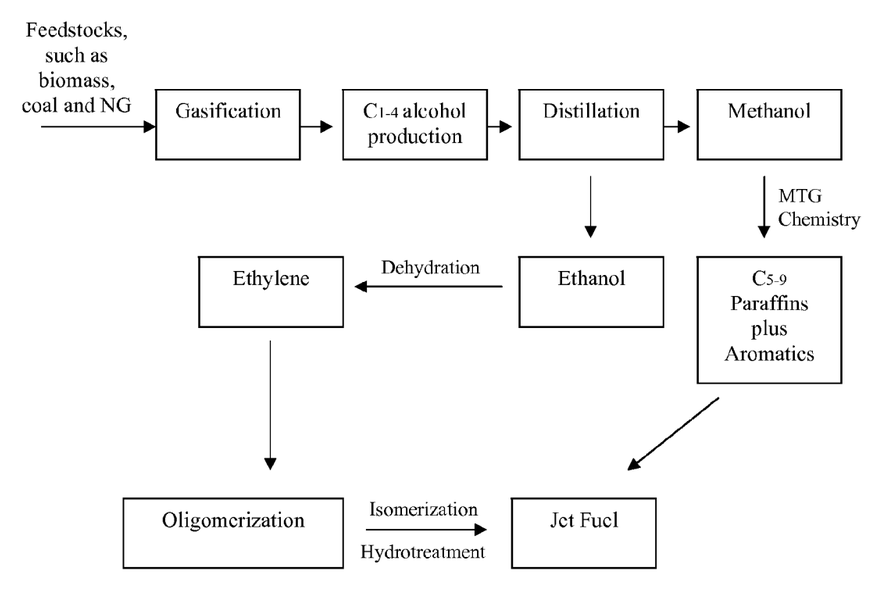
FIG. 1 is a block-flow diagram depicting an exemplary process for conversion of syngas to methanol and ethanol, conversion of methanol to paraffins and aromatics, conversion of ethanol into ethylene, conversion of ethylene into oligomers, and optional hydrotreatment and/or isomerization of the oligomers, according to some embodiments of the invention.

The present invention will now be further described by reference to the FIGURES. This exemplary detailed description illustrates by way of example, not by way of limitation, the principles of the invention.

In FIG. 1, a process block-flow diagram is depicted for various processes of the invention.

FIG. 1 is a block-flow diagram depicting an exemplary process for conversion of syngas to methanol and ethanol, conversion of methanol to dimethyl ether, according to some embodiments of the invention. In this variation, a starting syngas stream is provided (e.g., produced from biomass or otherwise received). The starting syngas stream is converted to a product mixture including $C_{1-4}$ alcohols. The product mixture is then divided into at least two streams, with a first stream comprising predominantly methanol, and a second stream comprising predominantly ethanol and higher alcohols. The methanol is converted to dimethyl ether, and the dimethyl ether is then converted to jet fuel range components. The ethanol and higher alcohols are dehydrated to form olefins, which are subjected to oligomerization conditions. The oligomers, which can optionally be isomerized and/or hydrotreated, are then combined with some or all of the products produced by reaction of the dimethyl ether.

I. Syngas Production

The syngas can be produced from biomass, but that is not necessary for this invention. Other sources of syngas include, for example, natural gas, coal, crude oil, and any other carbonaceous material.

In some embodiments, the syngas provided or generated for methods of this invention is produced from one or more carbon-containing feedstocks selected from timber harvesting residues, softwood chips, hardwood chips, tree branches, tree stumps, leaves, bark, sawdust, paper pulp, corn stover, wheat straw, rice straw, sugarcane bagasse, switchgrass, miscanthus, animal manure, municipal solid waste, municipal sewage, commercial waste, used tires, grape pumice, almond shells, pecan shells, coconut shells, coffee grounds, grass pellets, hay pellets, wood pellets, cardboard, paper, plastic, rubber, cloth, coal, lignite, coke, lignin, and/or petroleum. Mixtures of any of these feedstocks can be used.

Syngas can be produced by any known means, such as by one or more of gasification, pyrolysis, devolatilization, steam reforming, and partial oxidation of one or more feedstocks recited herein.

The syngas-generation unit or step may be a gasifier, such as a fluidized-bed gasifier. In variations, the gasifier type may be entrained-flow slagging, entrained flow non-slagging, transport, bubbling fluidized bed, circulating fluidized bed, or fixed bed. Some embodiments employ known gasification catalysts. "Gasification" and "devolatilization" generally refer herein to the reactive generation of a mixture of at least CO, $CO_2$, and $H_2$, using oxygen, air, and/or steam as the oxidant(s).

In some embodiments, syngas is produced by the methods taught in U.S. patent application Ser. No. 12/166,167, entitled "METHODS AND APPARATUS FOR PRODUCING SYNGAS," filed Jul. 1, 2008.

Gasification is known as the art to convert a variety of feedstocks, such as coal, methane, methanol, ethanol, glycerol, biomass such as corn stover, switchgrass, sugar cane bagasse, sawdust, and the like, black liquor, municipal solid waste, and lignin to synthesis gas. Many gasifiers have been developed, and one exemplary gasifier is that sold by TCG Energy (www.tcgenergy.com). Another gasifier of noteable mention is the Thermoselect (www.iwtonline.com). Also, see, for example, [http://www.biocap.ca/files/biodiesel/dalai.pdf]. The Wiley gasifier, covered by one or more of U.S. Pat. Nos. 7,638,070; 7857,995; 7,968,006; 8,017,040; 8,017,041 and 8,021,577 can also be used.

The water-gas-shift reaction plays an important role in the conversion of certain of these feedstocks to hydrogen via steam gasification and pyrolysis. Catalytic steam gasification can give high yields of syngas at relatively low temperatures. Biomass can be converted to syngas using a variety of known methods, including thermal gasification, thermal pyrolysis and steam reforming, and/or hydrogasification each of which can produce syngas yields of 70-75% or more.

These approaches are well known in the art, and need not be described in more detail. Gasification of coal was used in England and in the United States to produce "town gas" to light the city streets over a hundred years ago. The German war effort was fueled by coal gasification during World War II. Currently over 40% of South African motor fuel is derived from coal gasification, as well as 100% of their aviation fuel. Major suppliers of gasification technology include Sasol Lurgi, GE, Conoco-Phillips, and Shell with dozens of large, expensive plants operating worldwide.

In the U.S. a large gasification plant is producing synthetic natural gas in North Dakota, and two integrated combined cycle (IGCC) demonstration plants are generating Electricity—one in Florida and the other in Indiana. Eastman Chemical's coal gasification plant located in Tennessee once produced all Kodak film for the photography industry. It has operated successfully for over 25 years and continues to produce methanol, plastics, and other products for the chemical industry. Gasification is accomplished with heat, pressure, and the injection of ionized water.

The basic chemical reaction used in gasification is $C+H_2=CO+H_2$. This process begins in a heated, oxygen-starved environment (known as the pyrolysis chamber), which drives off moisture and volatile gases contained in the feedstock. Pyrolysis produces carbon char and ash that moves into a separate, externally heated gasification reactor, which converts the solid carbon molecule into a gaseous state. Next, in TCG's process ionized water is injected in a process known as steam reformation to create a water shift reaction to produce Syngas. The hot Syngas is water quenched and cleansed of its impurities in a proprietary, ionized water treatment system, thus delivering a clean, dry Syngas with no liquid discharge from the plant operation. It is important to note that the TCG process is not a typical gasification process, which requires the injection of oxygen for the reaction: $2C+O2+H2O=CO+H2+CO2$, nor is it heated by internal feedstock combustion which is represented by $C+O2=CO2$. Conventional gasification plants produce high amounts of carbon dioxide in their internal combustion processes. The externally heated TCG process actually reduces $CO_2$ through the following reaction: $CO_2+C=2CO$ and does not produce harmful combustion by-products. The other gasifier that has received some merit is the Thermochem gasifier that uses a pulse system to make syngas, which leaves many others to make the syngas in the correct ratio to produce various chemicals and fuels.

Syngas Cleanup

Syngas is converted to methanol by contact with a suitable catalyst under reactive conditions. Depending on the quality of the syngas, it may be desirable to purify the syngas prior to the methanol-generating reactor to remove carbon dioxide produced during the syngas reaction, and any sulfur compounds, if they have not already been removed. This can be accomplished by contacting the syngas with a mildly alkaline solution (e.g., aqueous potassium carbonate) in a packed column. This process can also be used to remove carbon dioxide from the product stream.

One example of a suitable syngas cleanup process is called extractive Merox. Merox is an acronym for mercaptan oxidation. It is a proprietary catalytic chemical process developed by UOP, and used in oil refineries and natural gas processing plants to remove mercaptans from a variety of products, including syngas, LPG, propane, butanes, light naphthas, kerosene and jet fuel by converting them to liquid hydrocarbon disulfides.

The Merox process requires an alkaline environment which, in some of the process versions, is provided by an aqueous solution of sodium hydroxide (NaOH), a strong base, commonly referred to as caustic. In other versions of the process, the alkalinity is provided by ammonia, which is a weak base.

The overall chemical reaction can be generalized as follows:

$$4RSH+O_2 \rightarrow 2RSSR+2H_2O$$

The catalyst in some versions of the process is a water-soluble liquid, such as methanol. In other versions, the catalyst is impregnated onto charcoal granules.

The Merox process is usually more economical than using a catalytic hydrodesulfurization process for much the same purpose, though the latter can be used if desired.

Water-Gas Shift Chemistry

Biomass gasification typically produces a synthesis gas with an approximately 1/1 ratio of hydrogen to carbon monoxide. It is generally desirable to have a 2/1 ratio of hydrogen to carbon monoxide when carrying out methanol synthesis. Accordingly, it is important to increase the amount of hydrogen in the syngas. This is typically done using water-gas shift chemistry, which involves reacting water with carbon monoxide to produce hydrogen and carbon dioxide. The general reaction is shown below:

II. Syngas Conversion to $C_{1-4}$ Alcohols

Syngas can be efficiently converted to methanol according to well-known techniques known in the art. Carbon monoxide and hydrogen react over commercially available catalysts to produce methanol. Today, a widely used catalyst is a mixture of copper, zinc oxide, and alumina first used by ICI in 1966. At 50-100 atm and 250 C, the production of methanol from carbon monoxide and hydrogen proceeds with high selectivity.

Syngas can be selectively converted to mixed $C_{1-4}$ alcohols by means of a chemical catalyst, such as described in U.S. patent application Ser. No. 12/166,203, entitled "METHODS AND APPARATUS FOR PRODUCING ALCOHOLS FROM SYNGAS."

Any suitable catalyst or combination of catalysts may be used in reactors for producing alcohols. Suitable catalysts may include, but are not limited to, one or more of ZnO/$Cr_2O_3$, Cu/ZnO, Cu/ZnO/$Al_2O_3$, Cu/ZnO/$Cr_2O_3$, Cu/$ThO_2$, Co/Mo/S, Co/S, Mo/S, Ni/S, Ni/Mo/S, Ni/Co/Mo/S, Rh, Ti, Fe, Ir, and any of the foregoing in combination with Mn and/or V. The addition of basic promoters (e.g. K, Li, Na, Rb, Cs, and Fr) increases the activity and selectivity of some of these catalysts for alcohols. Basic promoters include alkaline-earth and rare-earth metals. Non-metallic bases can also serve as effective promoters, in some embodiments.

In one embodiment, a catalyst is selected from the Group VI metals, namely Cr, MO, W and mixtures thereof. Next, the selected metal is nanosized to a mean particle diameter (ND) of less than about 100 nm. Nanosizing the metal provides more surface area per unit volume of the metal, thereby enhancing the reaction rates. The nanosized metal catalyst can then be sulfided to enhance its resistance to the catalyst poisons that are normally present in syngas.

Nanosizing of the metal catalyst can be achieved by a variety of methods. One method of nanosizing is sonication of a carbonyl precursor of the metal. An example of nanosizing is found in the literature reference (Mdleleni et al. J. Amer. Chem. Soc. 120 6189-6190 (1998)). Catalyst-sulfiding can be achieved during or after the nanosizing procedure.

During the alcohol production from syngas production, the nanosized, sulfided Group VI metal catalyst can be unsupported, or supported on a high surface area support such as carbon, alumina, silica or the like. In either arrangement, the nanosized catalyst can be suspended in an inert solvent, such as a high molecular weight hydrocarbon solvent such as ethylflo-164, to form a slurry. Suspension of the nanosized catalyst allows excellent heat management during the thermal operations, and this in turn increases mixed alcohol product yield.

The syngas can then be passed through the catalyst slurry to produce alcohols in the product stream. The input syngas composition varies from $H_2/CO$ of 1/4 to 3/1 though other gaseous impurities may be present. In order to enhance reaction rates, additives that make the Group VI metal catalyst more susceptible to initial carbon monoxide attack are an embodiment. The operating temperature range is ideally from about 200 C to less than about 300 C. The operating pressure ranges is from about 500 to about 3000 psig. The space-time-yield (STY) of product mixed alcohols is ideally greater than about 0.4 gram product/gram catalyst/hr. In order to enhance catalyst life, a small amount of sulfur source can optionally be added either directly to the reaction vessel in which alcohols are being continuously produced, or to the incoming syngas stream.

By combining these steps, using a novel catalyst in a novel process efficiently produces mixed alcohols. In one embodiment of this invention, nanosized particles (MPD<100 nm) of molybdenum are produced by the sonication method and are suspended in a hydrocarbon solvent having a carbon chain length of 30. A sulfur source, being elemental sulfur itself, is added to the slurry. By contacting the slurry with a stream of carbon monoxide and hydrogen in 1/2 ratio at temperature in the range of about 250 to about 280 C and pressure in the range of about 500 to about 200 psig pressure, mixed alcohols can be produced in the product stream with STY surpassing 0.4 grams product/gram catalyst/hour.

The synthesis gas, after cooling and cleaning, is typically at a ratio that will vary from $H_2/CO$ of 1:1.2 to 1:2, although other gaseous impurities may be present. The gaseous material is ideally then compressed at approximately 100 F at a pressure from about 500 to about 1000 psig and passed through the catalysts described herein to produce mixed alcohols, ideally with STY surpassing 0.4 grams product/gram catalyst/hour.

The digestion of manure from all types of animals produces syngas, although manure from diaries and hog farms and feedlots have been targeted. The digestion process typically yields several more moles of methane than of carbon dioxide. A commercially-available partial oxidation unit then disassociates the methane gas. The syngas from the partial oxidation unit is expected to yield a 1:1 ratio of $H_2$ to CO. The gaseous material can be treated as described above.

A steam reformer, such as those found on a typical methanol plant, may be utilized with a recirculation of the hydrogen back into the process to be utilized for makeup heat as well as additional carbon monoxide being manufactured from the carbon dioxide through the hydrogen burner unit furnished by others in the process.

As used herein, the ratio of $C_1$ to $C_{2+}$ means the weight ratio of methanol to higher alcohols such as ethanol, propanols, butanols, and the like, taken as a whole. This number may be easily calculated by determining the weight fraction of methanol in the mixed alcohols.

It is desired that ethyl alcohol be a major product constituent, with the yield of methanol at a very small portion of the overall product. Under some conditions, alcohols may be obtained in about 95 percent per pass of the $H_2/CO$ syngas at any preferred ratio. The selectivity of the $C_2$ and other higher alcohols are preferred and should be obtained with this invention. The space velocity of the hourly rate that the $H_2/CO$ gas passes a given volume of catalyst in an hour's time (GHSV) is a measure of the volume of the hydrogen plus carbon monoxide gas at a standard temperature and pressure. The selectivity of the alcohols generally increases as the space velocity increases, however conversion of the carbon monoxide decreases as the space velocity increases. Some of these gases may be recycled in the reaction.

III. Distillation of Methanol from $C_{2-4}$ and Higher Alcohols

Methanol boils at 64.7 C (148.4 F), while ethanol boils at 78.4 C (173 F) and higher alcohols have even higher boiling points, so it is relatively straightforward to separate methanol from the higher alcohols. Distillation of these materials needs no further technical discussion, though it is worth noting that water might be removed from the mixtures before distillation to avoid problems associated with azeotropes.

Accordingly, a distillation unit with a suitable number of theoretical plates, as such is known to those of skill in the art, is used to separate the methanol from the ethanol and higher alcohols.

IV. Types of Reactors Used in the Processes Described Herein

Reactors for conversion of one or more alcohols to jet fuel components are any type of reactor suitable for carrying out alcohol-to-jet fuel chemistry described herein. In one embodiment, the reactors include one or more zeolite catalysts effective for conversion of alcohols to jet fuel components.

A "reactor" described herein may be any type of catalytic reactor suitable for the conversion of syngas to alcohol mixtures. A reactor may, for example, be any suitable fixed-bed reactor. In some variations, a reactor comprises tubes filled with one or more catalysts. Syngas passing through the tubes undergoes catalyzed reactions to form alcohols or other products.

The reactor for converting syngas into alcohols can be engineered and operated in a wide variety of ways. The reactor operation can be continuous, semicontinuous, or batch. Operation that is substantially continuous and at steady state is preferable. The flow pattern can be substantially plug flow, substantially well-mixed, or a flow pattern between these extremes. The flow direction can be vertical-upflow, vertical-downflow, or horizontal. A vertical configuration can be one embodiment.

Any "reactor" used herein can in fact be a series or network of several reactors in various arrangements. For example, in some variations, the reactor comprises a large number of tubes filled with one or more catalysts.

The catalyst phase can be a packed bed or a fluidized bed. The catalyst particles can be sized and configured such that the chemistry is, in some embodiments, mass-transfer-limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

Reactors can consist of a simple vessel or tank, which can be stirred or unstirred. In one embodiment, reactors are closed reaction vessels, to prevent loss of chemicals to the atmosphere. The reactions may be conducted batch-wise, continuously, or semi-continuously.

The reaction temperature, pressure, and residence time for each process step are each not regarded as critical, provided that overall conditions are suitable for a desired conversion.

In general, solid, liquid, and gas streams produced or existing within the process can be independently passed to subsequent steps or removed/purged from the process at any point. Also, any of the streams or materials present may be subjected to additional processing, including heat addition or removal, mass addition or removal, mixing, various measurements and sampling, and so forth.

In some embodiments, the process is controlled or adjusted to attain certain jet fuel properties. As is known, relevant jet fuel properties can include freezing point, flash point, energy content, water content, sediment content, ash content, sulfur content, nitrogen content, phosphorus content, pH, density, viscosity, and so on.

V. Zeolite and Molecular Sieve Catalysts

A "zeolite catalyst" as used herein includes molecular sieves and other equivalent functional forms.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. These materials have come to be known as "molecular sieves" and are utilized in a variety of ways to take advantage of these properties.

Molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation.

One type of cation may be exchanged either entirely or partially with another type of cation utilizing ion-exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of the zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449), zeolite ZS-20 (U.S. Pat. No. 3,972,983); zeolite ZSM-35 (U.S. Pat. No. 4,016,245); and zeolite ZSM-23 (U.S. Pat. No. 4,076,842), for example.

The $SiO_2/Al_2O_3$ ratio of a given zeolite is variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques.

VI. Conversion of Methanol to Dimethyl Ether

Dimethyl ether (DME), also known as methoxymethane, is the organic compound with the formula $CH_3OCH_3$. It is a colorless gas that is used as a precursor to gasoline-range hydrocarbons using the process described herein, though DME can act as a clean fuel when burned in engines properly optimized for DME, such as diesel engines.

After synthesis gas is converted into methanol as described above, subsequent methanol dehydration in the presence of a different catalyst (for example, silica-alumina) produces DME. As described, this is a two-step (indirect synthesis) process that starts with methanol synthesis and ends with DME synthesis (methanol dehydration). Ideally, this process is conducted using organic waste or biomass.

This process has been conducted at commercial scale (see, for example, Manfred Müller, Ute Hübsch, "Dimethyl Ether" in Ullmann's Encyclopedia of Industrial Chemistry, Wiley-VCH, Weinheim, 2005).

Alternatively, in one embodiment, DME is produced through direct synthesis, using a dual catalyst system that permits both methanol synthesis and dehydration in the same process unit, with no methanol isolation and purification (see, for example, P. S. Sai Prasad et al., Fuel Processing Technology, 2008, 89, 1281). In this embodiment, by eliminating the intermediate methanol synthesis stage, the process provides efficiency advantages and cost benefits relative to where the methanol is isolated.

In one embodiment, the catalysts and conditions are those described in U.S. Pat. No. 65,908,963 by Voss, Joensen, and Hansen, entitled "Preparation of fuel grade dimethyl ether" or Sofianos and Scurrell, 1991, "Conversion of synthesis gas to dimethyl ether over bifunctional catalytic systems," Ind. Eng. Chem. Res., 30 (11), pp. 2372-2378.

Both the one-step and two-step processes above are commercially available. Currently, there is more widespread application of the two-step process since it is relatively simple and start-up costs are relatively low.

VII. Conversion of Dimethyl Ether to Jet Fuel Components

The DME produced as described above is then further dehydrated over a zeolite catalyst, such as ZSM-5, to give a jet fuel-range hydrocarbons with 80% (by weight based on the organics in the product stream) $C_{5+}$ hydrocarbon products.

The catalyst, such as ZSM-5, is frequently deactivated by a carbon build-up ("coking") over time in converting methanol to gasoline. The catalyst can be re-activated by burning off the coke in a stream of hot (500° C. (930° F.)) air. However, the number of re-activation cycles is limited.

Representative catalysts and conditions are described, for example, in Kolesnichenko et al., "Synthesis of gasoline from syngas via dimethyl ether," Kinetics and Catalysis Volume 48, Number 6, 789-793, 2007, also published in Kinetika i Kataliz, 2007, Vol. 48, No. 6, pp. 846-850 by the same authors.

In this embodiment, Zeolite H-TsVM is loaded with palladium by different methods. The properties of the resulting catalysts in gasoline synthesis from syngas via dimethyl ether depend on the way in which palladium was introduced. The catalysts have been characterized by ammonia temperature-programmed desorption (TPD), temperature-programmed reaction with hydrogen, and X-ray photoelectron spectroscopy. According to ammonia TPD data, use of a palladium ammine complex instead of palladium chloride reduces the concentration of strong acid sites and raises the concentration of medium-strength acid sites, thereby reducing the yield of $C_{1-4}$ hydrocarbons and increasing the yield of hydrocarbons in the jet fuel range. At T=340° C., P=100 atm, and GHSV=2000 h−1, the dimethyl ether conversion is 98-99%, the selectivity for hydrocarbons in the jet fuel range is >60%, the isoparaffin content of the product is ~61%, and the arene content is not higher than 29%.

Additional catalysts and conditions are described in U.S. Pat. No. 4,011,275 by Zahner, entitled "Conversion of modified synthesis gas to oxygenated organic chemicals," and U.S. Pat. No. 4,098,809 by Pagani, entitled "Process for the production of dimethyl ether."

Additional catalysts are well known to those of skill in the art, and the process described herein is not limited to the catalysts specifically mentioned herein.

VIII. Dehydration of Ethanol and Higher Alcohols

Ethanol can be dehydrated using known chemistry. In one embodiment, mixtures of ethanol and an aqueous acid, such as hydrochloric or sulfuric acid, are heated, and ethylene is evolved. This is an equilibrium reaction, and low pressure favors ethylene over ethanol.

Ethanol can also be dehydrated by passing it, in the vapor phase, over an acidic alumina catalyst. Suitable catalysts are known in the art.

IX. Oligomerization of Ethylene and Higher Olefins

There are several commercial processes which oligomerize ethylene to linear alpha olefins, any of which can be used. Several of these processes produce wide distributions of linear alpha olefins. These are the Ethyl Corporation (Ineos) process, Gulf (Chevron Phillips Chemical Company), Shell Oil Company SHOP process, the Idemitsu Petrochemical process and the SABIC-Linde α-Sablin process.

The α-Sablin process is a low-pressure ethylene oligomerization process conducted over heterogeneous catalyst in a slurry bed. The process also makes a $C_{4-20+}$ distribution of alpha-olefins.

Phillips (CP Chemical Company) ethylene trimerization process produces only 1-hexene. The IFP process dimerizes ethylene to high purity 1-butene. Mixtures of ethylene and butene and/or hexene can be subjected to further reactions, such as dimerization and/or trimerization, to produce hydrocarbons in the jet fuel range.

While the Ethyl process makes a Pseudo-Poisson distribution of products, most others, including the Sasol process, make a Schultz-Flory distribution.

Ineos (Ethyl) Process

The Ineos process is commonly called stoichiometric Ziegler process. It is a two-step process. In the first step, a stoichiometric quantity of triethyl aluminum in olefin diluent is reacted with excess ethylene at high pressure (above 1000 psig) and relatively low temperature (below 400° F.). On the average, nine moles of ethylene are added per mole of triethyl aluminum, resulting in, on average, a tri-octyl aluminum. The distribution of alkyl chains on the aluminum is determined by statistical bell curve distribution except for some smearing to the light side due to the kinetic phenomena and some smearing to the heavy side due to some incorporation of heavier olefins into the chain. Excess ethylene and olefin diluent are flashed off. The heavy aluminum tri-alkyls are reacted with ethylene again in a displacement or a transalkylation reaction, but at high temperature (over 400° F.) and at low pressure (less than 1000 psig) to recover triethyl aluminum and a statistical distribution of linear alpha olefins, which serve as the olefin diluent in the chain-growth step.

CP Chemicals (Gulf) Process

The Gulf linear alpha olefin process is commonly called a catalytic Ziegler process. Triethyl aluminum is used as a catalyst, but in catalytic amounts and the process is a single-step process. Tri-ethyl aluminum and excess ethylene are fed to a plug flow-reactor. The reaction is conducted at high pressure and high temperature. Excess ethylene is flashed off. The tri-ethyl aluminum catalyst is washed out of the product with caustic and the linear alpha olefins are separated. The product distribution is a Schultz-Flory distribution typical of catalytic processes.

In some embodiments, ethylene oligomerization yields olefins such as 1-butene, 1-hexene and 1-octene. These olefins can be combined with ethylene and subjected to olefin dimerization and/or trimerization reactions to provide hydrocarbons in the jet fuel range.

$C_{8-16}$ linear alpha olefins are in the desired jet fuel range, and can be subjected to isomerization and/or hydrotreatment steps.

Higher molecular weight olefins can be subjected to hydrocracking to provide additional material in the desired jet fuel range, or, alternatively, can be combined with lower molecular weight olefins and subjected to molecular averaging conditions to arrive at additional material in the desired jet fuel range.

During oligomerization processes, in addition to diesel cut products, products belonging to the gasoline fraction (boiling point lower than 180° C. and high octane number), can also be obtained.

During the oligomerization of olefins, the physical characteristics of the products obtained (cetane number, boiling point, viscosity, etc.) are greatly influenced by the branching degree of the products. If the catalyst used is not selective, the branching becomes considerable, which can be desirable for use in producing jet fuel components, in contrast to diesel fuel, where the branching would undesirably lower the cetane number in the diesel fuel. In one embodiment, a selective catalyst is used, and in another embodiment, a less selective catalyst is used.

One such selective zeolites is ZSM-5, and this zeolite is used in the MOGD process (Mobil Olefins to Gasoline and Distillate), as disclosed in U.S. Pat. No. 4,150,062 and U.S. Pat. No. 4,227,992. The products obtained from the reaction of butenes are trimers and tetramers, characterized by a low branching degree. The gas oil fraction however is lower than that of the jet fuel fraction. In order to provide butenes as feedstocks to this process, the ethylene can first be subjected to an olefin dimerization step.

Other zeolites with medium pores, ZSM-12, -23, etc. produce oligomers with a low branching degree due to the "shape selectivity" phenomenon. This is such that the gasoline cut, without aromatics, has a low octane number whereas the diesel cut has a high cetane number. Examples of the use of this type of material, for producing diesel fuel with a high cetane index, are provided in some recent patents of Mobil (U.S. Pat. No. 5,639,931; U.S. Pat. No. 5,780,703).

Amorphous acid materials (silico-aluminas), large pore zeolites, resins with cationic exchange and supported acids (e.g. phosphoric acid), on the other hand, produce oligomers with a high branching degree and a diesel cut with a low cetane number. All acid carriers supported with Ni also belong to a special category. This metal in fact is capable of competing with the acid sites of the carrier, reducing the isomerization reactions and forming oligomers with a low branching degree (JP 07309786), but at the same time favoring dimerization with respect to oligomerization to heavier products, creating products with a boiling point lower than that which distinguishes diesel cuts.

One example of a suitable olefin metathesis and oligomerization process uses modified ZSM-5 and ZSM-23, and is disclosed in PCT WO 93/06069.

Broken Hill has patented zeolites (ZSM-5, -11, -12) modified with >0.2% by weight of K, Na, Ca oxides (with respect to the weight of the catalyst, intended as zeolite plus ligand) in combined FCC and oligomerization systems (U.S. Pat. No. 4,675,460). In all the examples of the patent, the yield of the diesel fraction is lower than 28% by weight with respect to all the products obtained.

Neste OY has obtained products with a cetane number equal to 49 and a yield of the diesel fraction lower than 50% by weight in the presence of ZSM-5 doped with 0.01%-1% by weight of Ca (EP 0539126); or equal to 55 and a yield in the diesel fraction of less than 58% by weight with ZSM-5 doped with 1-3% by weight of Cr (WO 96/20988).

Eniricerche S.p.A. and Agip S.p.A. have disclosed (Italian Patent IT-1204005) an oligomerization process of light olefins carried out in the presence of a zeolite structurally similar to ZSM-5, titaniumaluminumsilicalite (Al-TS-1), which allows mixtures of olefins and aromatics having from 5 to 20 carbon atoms to be obtained, with a selectivity of over 87%.

By effecting the oligomerization reaction of olefins in the presence of a titaniumaluminumsilicalite in certain ratios and with an extra framework titanium oxide content of zero or below certain values, and operating at a high pressure, it is possible to obtain high yields of products with a high cetane number, suitable as fuels for diesel engines, in which the aromatic hydrocarbons are either substantially absent or present in a very limited quantity.

One representative process, starting from ethylene, involves oligomerizing ethylene in the presence of synthetic zeolites containing silicon, titanium and aluminum oxides, having a molar ratio $SiO_2/Al_2O_3$ ranging from 100 to 300, in one embodiment from 200 to 300, a molar ratio $SiO_2/TiO_2$ greater than 41, in one embodiment equal to or greater than 46, and a extra framework titanium oxide content which is zero or less than 25% by weight, in one embodiment zero or at the most less than 5%, with respect to the whole titanium oxide present, at a temperature ranging from 180 to 300° C., in one embodiment from 200 to 250° C., at a pressure greater than 40 atm, in one embodiment ranging from 45 to 80 atm. and a WHSV space velocity equal to or greater than 1 $h^{-1}$, in one embodiment ranging from 1.5 to 3 $h^{-1}$, in order to obtain a stream essentially consisting of oligomerized $C_5$-$C_{24}$ hydrocarbons. The resulting stream can be distilled to separate a $C_{5-15}$ fraction, if Jet-B type fuels are desired, or a $C_{8-16}$ fraction, if Jet-A, Jet A-1, or JP8-type fuels are desired. The oligomers can then optionally be isomerized and/or hydrogenated. A process of this type is described, for example, in U.S. Pat. No. 7,678,954.

Additional conditions for oligomerizing ethylene include those described in:

Zhang, et. al., "Oligomerization of Ethylene in a Slurry Reactor using a Nickel/Sulfated Alumina Catalyst", Ind. Eng. Chem. Res., 1997, 36, 3433-3438

U.S. Pat. No. 8,021,620

U.S. Pat. No. 8,093,439

X. Distillation of Oligomers to Isolate Jet Fuel Range Hydocarbons

The oligomers obtained by oligomerizing ethylene can be distilled, and products in the desired boiling point and/or molecular weight ranges can be obtained.

The paraffinic, olefinic, cyclic and/or aromatic compounds obtained by reacting dimethyl ether over a zeolite catalyst can also be distilled, and products in the desired boiling point and/or molecular weight ranges can be obtained.

Conditions for distilling hydrocarbons are well known to those of skill in the art.

XI. Optional Isomerization Conditions

Optionally, various fractions are isomerized. The isomerization products have more branched paraffins, thus improving their pour, cloud and freeze points. Isomerization processes are generally carried out at a temperature between 200° F. and 700° F., in one embodiment 300° F. to 550° F., with a liquid hourly space velocity between 0.1 and 2, in one embodiment between 0.25 and 0.50. The hydrogen content is adjusted such that the hydrogen to hydrocarbon mole ratio is between 1:1 and 5:1. Catalysts useful for isomerization are generally bifunctional catalysts comprising a hydrogenation component (in one embodiment selected from the Group VIII metals of the Periodic Table of the Elements, and in one embodiment selected from the group consisting of nickel, platinum, palladium and mixtures thereof) and an acid component. Examples of an acid component useful in the isomerization catalyst include a crystalline zeolite, a halogenated alumina component, or a silica-alumina component. Such paraffin isomerization catalysts are well known in the art.

XII. Optional Hydrotreatment Conditions

Optionally, the product from the oligomerization step, the isomerization step, and/or the step following conversion of the dimethyl ether to products over a zeolite catalyst is hydrogenated. The hydrogen can come from a separate hydrogen plant, can be derived from syngas, or can be made directly from methane and other light hydrocarbons.

After hydrogenation, which typically is a mild hydrofinishing step, the resulting distillate fuel product is highly paraffinic. Hydrofinishing is done after isomerization. Hydrofinishing is well known in the art and can be conducted at temperatures between about 190° C. to about 340° C., pressures between about 400 psig to about 3000 psig, space velocities (LHSV) between about 0.1 to about 20, and hydrogen recycle rates between about 400 and 1500 SCF/bbl.

The hydrofinishing step is beneficial in preparing an acceptably stable distillate fuels. Distillate fuels that do not receive the hydrofinishing step may be unstable in air and light due to olefin polymerization. To counter this, they may require higher than typical levels of stability additives and antioxidants.

XIII. Jet Fuel Compositions

In one embodiment, the invention relates to compositions, including jet fuel compositions, and compositions comprising components of jet fuel that can be blended with other components to produce jet fuel.

In one aspect of this embodiment, a jet fuel composition is provided in accordance with any of the processes described herein. Other variations provide per se novel jet fuel compositions, regardless of the process used to produce those compositions.

In one aspect of this embodiment, the compositions are capable of burning in a jet engine without need for being blended with conventional jet fuel. In another aspect of this embodiment, the compositions are blended with jet fuel, at concentrations between around 1 and around 99% by volume, around 10 and around 90% by volume, around 20 and around 80% by volume, around 30 and around 70% by volume, around 40 and around 60% by volume, and around 50% by volume. In this context, "around" means within 4%.

The various fractions obtained by distilling the products of the dimethyl ether conversion and the ethylene oligomerization (as well as oligomerization of olefins resulting from the dehydration of higher alcohols) can be combined. The combined products include hydrocarbons and aromatics in the jet fuel range. The exact combination of the products can vary, depending on the catalysts and conditions used to provide the various components, and the desired type of jet fuel to be produced.

The most commonly used fuels for commercial aviation are Jet A and Jet A-1 which are produced to a standardized international specification. The only other jet fuel commonly used in civilian turbine-engine powered aviation is Jet B which is used for its enhanced cold-weather performance. JP-8 is the jet fuel commonly used by the military.

Jet fuel is a mixture of a large number of different hydrocarbons. The range of their sizes (molecular weights or carbon numbers) is restricted by the requirements for the product, for example, the freezing point or smoke point. Kerosene-type jet fuel (including Jet A and Jet A-1) has a carbon number distribution between about 8 and 16 carbon numbers; wide-cut or naphtha-type jet fuel (including Jet B), between about 5 and 15 carbon numbers.

Differences Between Jet A and Jet A-1

Jet A specification fuel has been used in the United States since the 1950s, whereas Jet A-1 is the standard specification fuel used in the rest of the world. Both Jet A and Jet A-1 have a flash point higher than 38° C. (100° F.), with an autoignition temperature of 210° C. (410° F.).

The primary differences between Jet A and Jet A-1 are the higher freezing point of Jet A (−40° C. vs −47° C. for Jet A-1), and that Jet A-1 typically includes an anti-static additive.

Typical Physical Properties for Jet A and Jet A-1

Jet A-1 Fuel must meet the specification for DEF STAN 91-91 (Jet A-1), ASTM specification D1655 (Jet A-1) and IATA Guidance Material (Kerosine Type), NATO Code F-35.

Jet A Fuel must reach ASTM specification D1655 (Jet A) [5]

Typical physical properties for Jet A/Jet A-1 fuel:

|  | Jet A-1 | Jet A |
|---|---|---|
| Flash point | 42° C. | 51.1° C. |
| Autoignition temperature | 210° C. | 210° C. |
| Freezing point | −47° C. | −40° C. |
| Open air burning temperatures | 260-315° C. | 260-315° C. |
| Density at 15° C. | 0.804 kg/L | 0.820 kg/L |
| Specific energy | 43.15 MJ/kg | 43.02 MJ/kg |
| Energy density | 34.7 MJ/L | 35.3 MJ/L |

Jet B

Jet B is a fuel in the naphtha-kerosene region that is used for its enhanced cold-weather performance. A blend of approximately 30% kerosene and 70% gasoline, it is known as wide-cut fuel. It has a very low freezing point of −60 degrees Celsius and a low flash point as well. It is primarily used in US and some military aircraft.

Military Jet Fuel

Military organizations around the world use a different classification system of JP numbers. Some are almost identical to their civilian counterparts and differ only by the amounts of a few additives; Jet A-1 is similar to JP-8, Jet B is similar to JP-4. Other military fuels are highly specialized products and are developed for very specific applications. JP-5 fuel is fairly common, and was introduced to reduce the risk of fire on aircraft carriers (JP-5 has a higher flash point—a minimum of 60° C.). Other fuels were specific to one type of aircraft. JP-6 was developed specifically for the XB-70 Valkyrie and JP-7 for the SR-71 Blackbird. Both these fuels were engineered to have a high flash point to better cope with the heat and stresses of high speed supersonic flight. One aircraft-specific jet fuel still in use by the United States Air Force is JPTS, which was developed in 1956 for the Lockheed U-2 spy plane.

Jet fuels are sometimes classified as kerosene or naphtha-type. Kerosene-type fuels include Jet A, Jet A-1, JP-5 and JP-8. Naphtha-type jet fuels, sometimes referred to as "wide-cut" jet fuel, include Jet B and JP-4.

JP-8, or JP8 (for "Jet Propellant 8") is a jet fuel, specified and used widely by the US military. It is specified by MIL-DTL-83133 and British Defence Standard 91-87, and similar to commercial aviation's Jet-A.

JP-8+100 (F-37) is a version of JP-8 with an additive that increases its thermal stability by 56° C. (a difference of 100° F.). The additive is a combination of a surfactant, metal deactivator, and an antioxidant.

Additives

The DEF STAN 91-91 (UK) and ASTM D1655 (international) specifications allow for certain additives to be added to jet fuel, including:

Antioxidants to prevent gumming, usually based on alkylated phenols, e.g., AO-30, AO-31, or AO-37;

Antistatic agents, to dissipate static electricity and prevent sparking; Stadis 450, with dinonylnaphthylsulfonic acid (DINNSA) as the active ingredient, is an example Corrosion inhibitors, e.g., DCI-4A used for civilian and military fuels, and DCI-6A used for military fuels;

Fuel System Icing Inhibitor (FSII) agents, e.g., Di-EGME; FSII is often mixed at the point-of-sale so that users with heated fuel lines do not have to pay the extra expense.

Biocides are to remediate microbial (i.e., bacterial and fungal) growth present in aircraft fuel systems. Currently, two biocides are approved for use by most aircraft and turbine engine original equipment manufacturers (OEMs); Kathon FP1.5 Microbiocide and Biobor JF.

Metal deactivator can be added to remediate the deleterious effects of trace metals on the thermal stability of the fuel. The one allowable additive is N,N'-disalicylidene 1,2-propanediamine.

Additional additives include jet fuel ignition improvers, jet fuel stability improvers, jet fuel corrosion inhibitors, jet fuel detergent additives, jet fuel cold flow improvers, jet fuel combustion improvers, jet fuel luminosity (particulate) reducers/radiation quenchers, jet fuel antimicrobial/antifungal adjuncts, jet fuel antistats, jet fuel smoke mitigators, other conventional jet fuel adjuncts and mixtures thereof.

Such additives are known in the fuel-making art, see for example Kirk Othmer, Encyclopedia of Chemical Technology, Wiley, N.Y., 4th Ed., Vol. 3., pp. 788-812 (1992) and Vol. 12, pp. 373-388 (1994) and references therein. Percentages and proportions can be adjusted within ranges well known to formulators.

XIV. Miscellaneous

It can be difficult to obtain sufficient biomass to carry out the chemistry using a conventional reactor. In one embodiment, one or more of the process steps is carried out using a micro-fluidic reactor or microchannel reactor. The reactor can include a heat exchanger, which can include a plurality of heat exchange channels adjacent to the process microchannels. In one embodiment, the heat exchange channels are microchannels.

In one aspect of this embodiment, the microchannel reactor includes at least one process microchannel, the process microchannel having an entrance and an exit; and at least one heat exchange zone adjacent to the process microchannel, the heat exchange zone comprising a plurality of heat exchange channels. The heat exchange channels can extend lengthwise at right angles relative to the lengthwise direction of the process microchannels. The heat exchange zones can extend lengthwise in the same direction as the process microchannels, and can be positioned near the process microchannel entrance. The length of the heat exchange zone is ideally less than the length of the process microchannel. The width of the process microchannel at or near the process microchannel exit is ideally greater than the width of the process microchannel at or near the process microchannel entrance. In one embodiment, the at least one heat exchange zone includes a first heat exchange zone and a second heat exchange zone, where the length of the second heat exchange zone being less than the length of the first heat exchange zone.

In one aspect of this embodiment, the process microchannels are characterized by having a bulk flow path. The term "bulk flow path" refers to an open path (contiguous bulk flow region) within the process microchannels. A contiguous bulk flow region allows rapid fluid flow through the microchannels without large pressure drops. The flow of fluid in the bulk flow region can be laminar. Bulk flow regions within each process microchannel can have a cross-sectional area of about 0.05 to about 10,000 mm$^2$, and in one embodiment, about 0.05 to about 5000 mm$^2$, and in another embodiment, about 0.1 to about 2500 mm$^2$. The bulk flow regions can include from about 5% to about 95%, and in one embodiment, include from about 30% to about 80%, of the cross-section of the process microchannels.

The contact time of the reactants with the catalyst within the process microchannels typically ranges up to about 2000 milliseconds (ms), and in one embodiment, from about 10 ms to about 1000 ms, and in another embodiment, from about 20 ms to about 500 ms. In one embodiment, the contact time may range up to about 300 ms, and in another embodiment, from about 20 to about 300 ms, and in a further embodiment from about 50 to about 150 ms.

The space velocity (or gas hourly space velocity (GHSV)) for the flow of the reactant composition and product through the process microchannels is typically at least about 1000 hr$^{-1}$ (normal liters of feed/hour/liter of volume within the process microchannels) or at least about 800 ml feed/(g catalyst) (hr). The space velocity typically ranges from about 1000 to about 1,000,000 hr$^{-1}$, or from about 800 to about 800,000 ml feed/(g catalyst) (hr). In one embodiment, the space velocity ranges from about 10,000 to about 100,000 hr$^{-1}$, or about 8,000 to about 80,000 ml feed/(g catalyst) (hr).

The temperature of the reactant composition entering the process microchannels typically ranges from about 150° C. to about 400° C., and in one embodiment is between about 180° C. to about 350° C., and in another embodiment, is from about 180° C. to about 325° C.

The temperature of the reactant composition and product within the process microchannels may range from about 200° C. to about 400° C., and in one embodiment is from about 220° C. to about 370° C.

The temperature of the product exiting the process microchannels typically ranges from about 200° C. to about 400° C., and in one embodiment is from about 320° C. to about 370° C.

The pressure within the process microchannels is typically between about 5 and 50 atmospheres, more typically, 10 to about 50 atmospheres, and in one embodiment from about 10 to about 30 atmospheres, and in one embodiment from about 10 to about 25 atmospheres, and in one embodiment from about 15 to about 25 atmospheres.

The pressure drop of the reactants and/or products as they flow through the process microchannels can range up to about 10 atmospheres per meter of length of the process microchannel (atm/m), and in one embodiment, up to about 5 atm/m, and in one embodiment up to about 3 atm/m.

The reactant composition entering the process microchannels is typically in the form of a vapor, while the product exiting the process microchannels may be in the form of a vapor, a liquid, or a mixture of vapor and liquid. The Reynolds Number for the flow of vapor through the process microchannels is typically in the range of about 10 to about 4000, and in one embodiment about 100 to about 2000. The Reynolds Number for the flow of liquid through the process microchannels is typically about 10 to about 4000, and in one embodiment about 100 to about 2000.

The heat exchange fluid entering the heat exchange channels may be at a temperature of about 150° C. to about 400° C., and in one embodiment about 150° C. to about 370° C. The heat exchange fluid exiting the heat exchange channels may be at a temperature in the range of about 220° C. to about 370° C., and in one embodiment about 230° C. to about 350° C. The residence time of the heat exchange fluid in the heat exchange channels typically ranges from about 50 to about 5000 ms, and in one embodiment, about 100 to about 1000 ms. The pressure drop for the heat exchange fluid as it flows through the heat exchange channels may range up to about 10 atm/m, and in one embodiment from about 1 to about 10 atm/m, and in one embodiment from about 2 to about 5 atm/m. The heat exchange fluid may be in the form of a vapor, a liquid, or a mixture of vapor and liquid. The Reynolds Number for the flow of vapor through the heat exchange channels is typically from about 10 to about 4000, and in one embodiment about 100 to about 2000. The Reynolds Number for the flow of liquid through heat exchange channels may be from about 10 to about 4000, and in one embodiment about 100 to about 2000.

The conversion of dimethyl ether to products is ideally at least about 40% or higher per cycle, and in one embodiment about 50% or higher, and in one embodiment about 55% or higher, and in one embodiment about 60% or higher, and in one embodiment about 65% or higher, and in one embodiment about 70% or higher. The term "cycle" is used herein to refer to a single pass of the reactants through the process microchannels.

The yield of products is ideally about 25% or higher per cycle, and in one embodiment about 30% or higher, and in one embodiment about 40% or higher per cycle.

Using the microchannel reactors described herein, one can efficiently control the heat generated from one or more of the exothermic methanol-to-gasoline, methanol-to-olefin, and olefin oligomerization reactions. Ideally, using the microfluidic approach, it may be possible to carry out the entire synthesis, and only isolate products, such as unreacted syngas, methanol, dimethyl ether, and/or the products of the dimethyl ether-to-gasoline chemistry, as the products exit the microchannel reactor.

All patents and publications disclosed herein are hereby incorporated by reference in their entirety and for all purposes. Modifications and variations of the present invention, related to an alternative fuel composition, and blends of the alternative fuel composition with gasoline, will be obvious to those skilled in the art from the foregoing detailed description of the invention. Jet fuel and other fuels are expected to become a part of this patent, along with mixed alcohols produced using a molybdenum sulfide catalyst.

The present invention has utility with respect to biorefinery concepts. Final product mixes from a biorefinery can be optimized for maximum profitability and/or minimum carbon footprint, for example, by known techniques. Some embodiments of the invention can reduce overall energy intensity and/or reduce the number of processing steps to manufacture renewable jet fuel.

All publications, patents, and patent applications cited in this specification are incorporated herein by reference in their entirety as if each publication, patent, or patent application was specifically and individually put forth herein. All ASTM specifications recited herein are also incorporated by reference.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent that there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing jet fuel components, comprising:
   a) generating or providing syngas;
   b) converting the syngas using an alcohol-synthesis catalyst to a first stream comprising methanol, ethanol, and, optionally, higher alcohols;
   c) separating the methanol from the ethanol and, optionally, higher alcohols,
   d) converting at least some of the methanol to dimethyl ether,
   e) converting the dimethyl ether to one or more jet fuel range hydrocarbons and aromatics using a zeolite catalyst,
   f) dehydrating the ethanol and, optionally, higher alcohols to form ethylene and, optionally, higher olefins,
   g) oligomerizing the ethylene and, optionally, higher olefins to produce olefins in the jet fuel range,
   h) optionally hydrogenating and/or isomerizing the olefins in the jet fuel range to form paraffins in the jet fuel range, and
   i) combining one or more products from step c) with one or more of the products of step h).

2. The process of claim 1, wherein said syngas is derived from biomass.

3. The process of claim 1, wherein the ethanol and optionally higher alcohols comprises $C_3$ and $C_4$ alcohols.

4. The process of claim 1, wherein said jet fuel components include at least one $C_5$-$C_{10}$ hydrocarbon.

5. The process of claim 1, wherein at least some of said jet fuel components are hydrotreated.

6. The process of claim 1, wherein at least some of said jet fuel components are further subjected to isomerization.

7. The process of claim 1, further comprising blending said jet fuel components as a blendstock with JP8, JPA, JP4, or JP1.

* * * * *